United States Patent [19]

Pilotto et al.

[11] Patent Number: 4,761,399
[45] Date of Patent: Aug. 2, 1988

[54] DIPEPTIDE COMPOUNDS HAVING PHARMACEUTICAL ACTIVITY AND COMPOSITIONS CONTAINING THEM

[75] Inventors: Alberto Pilotto; Mario Portelli, both of Vicenza; Angelo Carenzi, Busto Arsizio; Davide Della Bella, Milan, all of Italy

[73] Assignee: Zambon S.p.A., Vicenza, Italy

[21] Appl. No.: 874,179

[22] PCT Filed: Oct. 16, 1985

[86] PCT No.: PCT/EP85/00543
§ 371 Date: Aug. 11, 1986
§ 102(e) Date: Aug. 11, 1986

[87] PCT Pub. No.: WO86/02353
PCT Pub. Date: Apr. 24, 1986

[30] Foreign Application Priority Data

Oct. 16, 1984 [IT] Italy ................................ 23173 A/84

[51] Int. Cl.⁴ .................... C07D 277/06; A61K 31/41
[52] U.S. Cl. ...................................... 514/19; 548/200
[58] Field of Search .......................... 548/200; 514/19

[56] References Cited

PUBLICATIONS

Dubini, Chemical Abstracts, vol. 95, #1257846 (1981).

Primary Examiner—Robert Gersil
Attorney, Agent, or Firm—Stevens, Davis, Miller & Mosher

[57] ABSTRACT

The compounds of formula

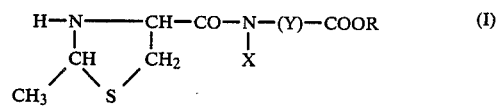

wherein the group

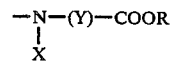

represents the residue of a natural amino acid selected from the group consisting of glycine, alanine, beta-alanine, phenylalanine, isoleucine, methionine, proline, aspartic acid and arginine; R represents a hydrogen atom or a $C_1$–$C_4$ alkyl; and their acid-addition salts with pharmaceutically acceptable organic or inorganic acids; are useful in the preventive and curative treatment of pathologic syndromes due to the lowering of glutathione (GSH) levels.

8 Claims, No Drawings

DIPEPTIDE COMPOUNDS HAVING PHARMACEUTICAL ACTIVITY AND COMPOSITIONS CONTAINING THEM

The present invention relates to compounds having pharmaceutical activity and more particularly it concerns dipeptide compounds and their use in the preventive and curative treatment of pathologic syndromes deriving from low intracellular glutathione (GSH) levels.

The invention concerns also pharmaceutical preparations containing the dipeptides as an active ingredient.

An object of the invention are the compounds of formula

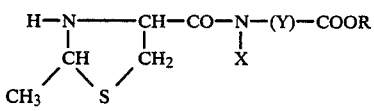

wherein the group

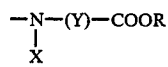

represents the residue of a natural amino acid selected from the group consisting of glycine, alanine, beta-alanine, phenylalanine, isoleucine, methionine, proline, aspartic acid and arginine; R represents a hydrogen atom or a $C_1$–$C_4$ alkyl; and their acid-addition salts with pharmaceutically acceptable organic or inorganic acids.

Specific examples of the compounds of formula I are:
(2-methyl-thiazolidin-4-carbonyl)-glycine and the esters thereof, of formula

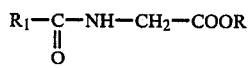

(2-methyl-thiazolidin-4-carbonyl)-alanine and the esters thereof, of formula

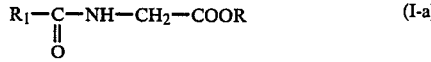

(2-methyl-thiazolidin-4-carbonyl)-beta-alanine and the esters thereof, of formula

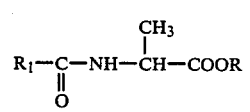

(2-methyl-thiazolidin-4-carbonyl)-phenylalanine and the esters thereof, of formula

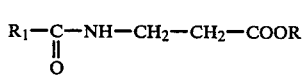

(2-methyl-thiazolidin-4-carbonyl)-isoleucine and the esters thereof, of formula

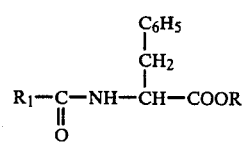

(2-methyl-thiazolidin-4-carbonyl)-methionine and the esters thereof, of formula

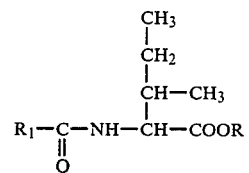

(2-methyl-thiazolidin-4-carbonyl)-proline and the esters thereof, of formula

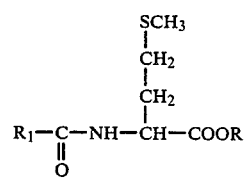

(2-methyl-thiazolidin-4-carbonyl)-aspartic acid and the esters thereof, of formula

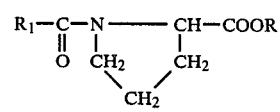

(2-methyl-thiazolidin-4-carbonyl)-arginine and the esters thereof, of formula

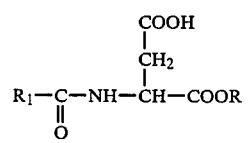

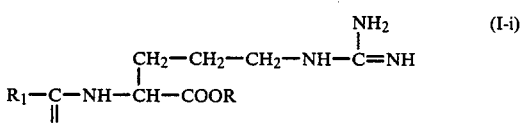

and the pharmaceutically acceptable salts thereof.

In the above compounds (I-a,i), $R_1$ is the group

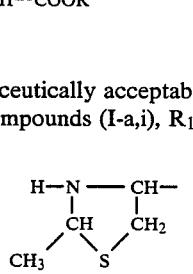

and R is a hydrogen atom or a $C_1$–$C_4$ alkyl.

The preparation of the compounds of formula I are carried out by condensing 2-methyl-thiazolidine-4-carboxylic acid, suitably protected on the nitrogen atom, with an ester of the selected amino acid in the presence of a coupling agent.

A suitable protecting group is, for example, the t-butoxycarbonyl group.

A coupling agent, dicyclohexylcarbodiimide in the presence of N-hydroxy-benzotriazole may be used.

By removal of the protecting group, the esters of formula I are obtained; from these, if desired, the free acids are obtained by hydrolysis.

Alternatively the hydrolysis may precede the removal of the protecting group on nitrogen atom of the 2-methyl-thiazolidine-4-carboxylic moiety.

When the amino acid to be condensed with 2-methyl-thiazolidine-4-carboxylic acid is aspartic acid or arginine it is advisable that the second carboxy group or respectively amino group of said amino acids, be protected.

The protection and the liberation of said groups is carried out according to methods known in the chemistry of amino acids. The preparation of the acid addition salts is carried out according to usual procedures.

It is evident to the expert in the field that the compounds of formula I have asymmetric carbon atoms and thus they exist in the form of various stereoisomers.

If desired, it is possible to separate the stereoisomers according to usual procedures both as final products and as intermediates. The single isomers as well as their mixture are comprised in the scope of the present invention.

The compounds of the invention have shown to be able to promote the reconstitution of the cellular content of glutathione (GSH) and to provide an effective protection against the cellular damages caused by endogenous as well as exogenous toxic factors. GSH is, at the intracellular level, the antidote physiologically appointed to the neutralization and thus detoxication, by the formation of covalent bonds, of highly reactive toxic substances of endogenous or exogenous origin.

Depletion in GSH involves the starting of cellular degeneration and necrosis processes (Larsson et al. eds., "Function of GSH", Raven Press, N.Y., 1983).

The compounds of the invention have shown to be endowed also with positive characteristics of bioavailability and general and local tolerability.

Thus, they are useful drugs suitable in the prevention and in the treatment of pathologic syndromes in which the aethiopathogenic origin is the depletion of GSH content in the parenchymal organs or in the mesenchymal cellular population, said depletion being due to interaction with methabolic intermediates having endogenous origin, for example toxinfective, as well as exogenous, for example exposure to noxious chemicals.

These syndromes may affect various organs and tissues and may be expressed as toxic or toxinfective hepatopathy, as sub-acute or chronic respiratory affection of infective origin (for example bronchitis) or due to inhalation of extraneous substances (for example in smokers), as arthritis, as central or peripheral neuropathy with degenerative components, as degenerative cardiopathy during chemotherapy.

The activity of the compounds of the invention on the intracellular GSH levels was tested on animals (mouse) in which a depletion of GSH was previously induced by treatment with p.acetamino-phenol (NAPA) in standard conditions.

The GSH levels in the animals liver were determined before the treatment with NAPA and 30 and 60 minutes thereafter (Mitchell J. R. et al., J. Pharmacol, Expl. Ther., 187, 185–194, 1973), according to a modification of the procedure described by Hissin et al. (Anal. Biochem., 74, 214–226, 1976).

All the tested compounds showed to be highly effective under the experimental conditions and in both oral and parenteral administration, after only 30 minutes a meaningful increase in the intracellular GSH level was observed with respect to previously untreated controls.

After 60 minutes, the GSH level was further increased reaching about 70% of that of witness mice.

The standard experimental test selected to demonstrate the protective characteristics of the compounds of invention against toxic substances in the sound animal was the test in which a lethal dose of NAPA is administered to the mouse (Alhava E. et al., Acta Pharmacol. et Toxicol., 42, 317–319, 1978).

The reduction of mortality was evaluated when the compound under examination was administered contemporaneously with the toxic substances or 2 hours thereafter.

The results obtained in these experiments showed how all the tested compounds, even if in different degrees, provide an effective protection both by oral and by parenteral administration.

From the evaluation of all the experimental results it is possible to conclude that the tested compounds are very effective in promoting the biosynthesis of intracellular GSH. In the test concerning the protection of the sound animal from the acute toxic effects of NAPA, this characteristic is particularly evident.

With respect to 2-methyl-thiazolidine-4-carboxylic acid used as such as reference compound, the compounds according to invention showed, in equimolecular amounts, a protective dose value, $PD_{50}$, form 3 to 6 times lower.

The protection ensured by administering an extemporaneous association of 2-methyl-thiazolidine-4-carboxylic acid and the respective amino acid was also lower than that obtained by administering an equimolecular amount of the corresponding compound of formula I. For example, the extemporaneous administration of 2-methyl-thiazolidine-4-carboxylic acid and arginine is practically uneffective.

By the point of view of pharmacological activity the preferred compounds of formula I are those in which the amino acid is in esterified form (R=alkyl), and in particular the compounds in which 2-methyl-thiazolidine-4-carboxylic acid is bonded by peptidic bond to methionine, beta-alanine or proline.

The tested compounds have also a good general and local tolerability in the selected administration ways: oral and parenteral.

In both cases, no secondary effect was evidenced in the mouse also after 72 hours from administration and with doses as high as 2 g/kg.

Another object of the present invention relates to pharmaceutical compositions containing as active ingredient a compound of formula I or an acceptable salt thereof.

Said compositions contain the active ingredient in association with an organic or inorganic, solid or liquid pharmaceutically acceptable carriers; according to the prescriptions, the compositions may be administered orally, parenterally, intramuscularly, intravenously or by inhalation.

The pharmaceutical preparations may be solid like tablets, pills, capsules, powders, granulates or liquid like solutions, suspensions, emulsions.

They may be prepared so as to ensure a time lasting release of the active ingredient after administration.

Beside the carriers, the compositions may also contain preservants, stabilizers, wetting agents, emulsifiers, salts to regulate the osmotic pressure, buffers, dyes, flavorings, etcetera.

The compositions, which may also contain other active ingredients, which are prepared according to conventional procedures.

The therapeutical dose to be administered depends on different factors such as the seriousness of the pathologic state, the selected administration way, the specific characteristics of the selected compound of formula I, etcetera.

Daily dosages comprised between 2 and 20 mg/kg (body weight) may be considered; as antidote in the case of acute poisoning, said doses may be increased up to 4-6 g in total.

With the scope of better illustrating the invention, the following examples are given.

EXAMPLE 1

Preparation of N-t.butoxycarbonyl-2-methyl-thiazolidine-4-carboxylic acid.

To a suspension of 2-methyl-thiazolidine-4-carboxylic acid (10 g, 67.9 mmol) in dimethylformamide (37 ml) kept under stirring at room temperature, tetramethylguanidine (17 ml, 135.8 mmol) was added.

The solution was cooled at 10°-15° C. and t.butoxycarbonylazide (14.6 g, 102 mmol) was slowly added.

After 48 hours at room temperature, the solution was evaporated to dryness under vacuum.

The solid residue was collected with ethyl acetate and the solution was washed with an aqueous solution of citric acid at 10% conc. and then with water.

The organic phase was dried on sodium sulphate then evaporated to dryness under vacuum.

The residue was collected with petroleum ether and the precipitate was filtered and dried.

N-t.butoxycarbonyl-2-methyl-thiazolidine-4-carboxylic acid (11.9 g) was thus obtained.

$[\alpha]_D^{20} = -70°$ (c=1, DMF)

m.p.=115°-116° C.

$R_f$=0.78 (AcOEt:Py:AcOH:H$_2$O=120:10:3:5.5)

EXAMPLE 2

Preparation of (2-methyl-thiazolidin-4-carbonyl)-glycine methyl ester hydrochloride.

To a solution of glycine methyl ester hydrochloride (4.57 g, 36.4 mmol) in dimethylformamide (100 ml) kept under stirring at −5° C., N-methyl-morpholine (4.01 ml, 36.4 mmol) and then a solution of N-t.butoxycarbonyl-2-methyl-thiazolidine-4-carboxylic acid (9 g, 36.4 mmol) in dimethylformamide (20 ml) were added.

To the resulting solution kept under stirring at −5° C., dicyclohexylcarbodiimide (9 g, 43.68 mmol) and N-hydroxy-benzotriazole (5.89 g, 43.68 mmol) were added.

After 24 hours under stirring at +4° C., the precipitate (dicyclohexylurea) was filtered and the filtrate was evaporated to dryness.

An oil was obtained which was dissolved in ethyl acetate and the solution was washed with an aqueous solution of citric acid at 10%, with an aqueous sodium bicarbonate solution at 10% and with water.

The organic solution, dried on sodium sulphate was evaporated to dryness under vacuum at 40° C.

(N-t.butoxycarbonyl-2-methyl-thiazolidine-4-carbonyl)-glycine methyl ester (9.48 g) was thus obtained as oil.

The obtained product (6.5 g) was treated at room temperature under nitrogen, with ethyl acetate (100 ml) containing 13% (w/v) of hydrogen chloride.

After 1 hour the solution was evaporated to dryness under vacuum at 35° C.

The residue, after crystallization from isopropyl alcohol, afforded (2-methyl-thiazolidine-4-carbonyl)-glycine methyl ester hydrochloride (4.7 g)

$[\alpha]_D^{20} = -80°$ (c=1, CH$_3$OH)

m.p.=75°-76° C.

$R_f$=0.8 (AcOEt:Py:AcOH:H$_2$O=120:10:3:5.5)

EXAMPLE 3

Preparation of (2-methyl-thiazolidine-4-carbonyl)-L-alanine methyl ester hydrochloride.

To a solution of L-alanine methyl ester hydrochloride (5.08 g, 36.4 mmol) in dimethylformamide (60 ml) kept under stirring at −5° C., N-methyl-morpholine (4.01 ml, 36.4 mmol) and then a solution of N-t.butoxycarbonyl-2-methyl-thiazolidine-4-carboxylic acid (9 g, 36.4 mmol) in dimethylformamide (20 ml) were added.

To the resulting solution kept under stirring at −5° C., dicyclohexylcarbodiimide (9 g, 43.68 mmol) and N-hydroxy-benzotriazole (5.89 g, 43.68 mmol) were added.

After 24 hours under stirring at +4° C., the precipitate (dicyclohexylurea) was filtered and the filtrate was evaporated to dryness.

An oil was obtained which was dissolved in ethyl acetate and the solution was washed with an aqueous solution of citric acid at 10%, with an aqueous sodium bicarbonate solution at 10% and with water.

The organic solution, dried on sodium sulphate was evaporated to dryness under vacuum at 40° C.

(N-t.butoxycarbonyl-2-methyl-thiazolidine-4-carbonyl)-L-alanine methyl ester (10.1 g) was thus obtained as oil.

The obtained product (8.2 g) was treated at room temperature under nitrogen, with ethyl acetate (100 ml) containing 13% (w/v) of hydrogen chloride.

After 1 hour the solution was evaporated to dryness under vacuum at 35° C.

The residue, after crystallization from isopropyl alcohol diethyl ether, afforded (2-methyl-thiazolidine-4-carbonyl)-L-alanine methyl ester hydrochloride (5.1 g) as raw product.

The product was purified by chromatography on a silica gel column (eluent ethyl acetate, pyridine, acetic acid, water in the ratio 120:10:3:5.5) and crystallized from ethyl acetate/petroleum ether.

$[\alpha]_D^{20} = -107°$ (c=1, CH$_3$OH)

m.p.=80°-81° C.

$R_f$=0.8 (AcOEt:Py:AcOH:H$_2$O=120:10:3:5.5)

EXAMPLE 4

Preparation of (2-methyl-thiazolidin-4-carbonyl)-beta-alanine methyl ester.

To a solution of beta-alanine methyl ester hydrochloride (5.08 g, 36.4 mmol) in dimethylformamide (35 ml) kept under stirring at −5° C., N-methyl-morpholine (4.01 ml, 36.4 mmol) and then a solution of N-t.butoxycarbonyl-2-methyl-thiazolidine-4-carboxylic acid (9 g, 36.4 mmol) in dimethylformamide (15 ml) were added.

To the resulting solution kept under stirring at −5° C., dicyclohexylcarbodiimide (9 g, 43.68 mmol) and N-hydroxy-benzotriazole (5.89 g, 43.68 mmol) were added.

After 24 hours under stirring at +4° C., the precipitate (dicyclohexylurea) was filtered and the filtrate was evaporated to dryness.

An oil was obtained which was dissolved in ethyl acetate and the solution was washed with an aqueous solution of citric acid at 10%, with an aqueous sodium bicarbonate solution at 10% and with water.

The organic solution, dried on sodium sulphate was evaporated to dryness under vacuum at 40° C.

(N-t.butoxycarbonyl-2-methyl-thiazolidine-4-carbonyl)-beta-alanine methyl ester (10.7 g) was thus obtained as oil.

The obtained product (7.9 g) was treated at room temperature under nitrogen, with ethyl acetate (90 ml) containing 13% (w/v) of hydrogen chloride.

After 1 hour the solution was evaporated to dryness under vacuum at 35° C.

The residue, after crystallization from isopropyl alcohol diethyl ether, afforded (2-methyl-thiazolidine-4-carbonyl)-beta-alanine methyl ester hydrochloride (5.4 g).

$[\alpha]_D^{20} = -85°$ (c=1, $CH_3OH$)
m.p.=124°-125° C.
$R_f$=0.74 (AcOEt:Py:AcOH:$H_2O$=120:10:3:5.5)

EXAMPLE 5

Preparation of (2-methyl-thiazolidine-4-carbonyl)-beta-alanine hydrochloride.

To a solution of (N-t.butoxycarbonyl-2-methyl-thiazolidine-4-carbonyl)-beta-alanine methyl ester (4.2 g, 12.6 mmol) in methanol (25 ml), 1N sodium hydroxide (25.2 ml, 25.2 mmol) was added at room temperature.

After 1.5 hours the solution was concentrated under vacuum at 40° C. and, after cooling at 0° C., it was acidified by citric acid up to pH 3.

(N-t.butoxycarbonyl-2-methyl-thiazolidine-4-carbonyl)-beta-alanine (2.93 g) precipitated, it was separated by filtration, washed with water and dried (m.p.=117°-118° C.).

The obtained product (1.55 g, 4.87 mmol) was dissolved, at room temperature and under nitrogen, in ethyl acetate (45 ml) containing 13% (w/v) of hydrogen chloride.

After 15 minutes diethyl ether was added and (2-methyl-thiazolidine-4-carbonyl)-beta-alanine (1.1 g) precipitated, it was collected by filtration, washed and dried.

$[\alpha]_D^{20} = -94°$ (c=1, $CH_3OH$)
$R_f$=0.38 (AcOEt:Py:AcOH:$H_2O$=120:10:3:5.5)

EXAMPLE 6

Preparation of (2-methyl-thiazolidin-4-carbonyl)-L-methionine methyl ester hydrochloride.

To a solution of L-methionine methyl ester hydrochloride (9.75 g, 48.8 mmol) in dimethylformamide (50 ml) kept under stirring at −5° C., N-methyl-morpholine (5.38 ml, 48.8 mmol) and then a solution of N-t.butoxycarbonyl-2-methyl-thiazolidine-4-carboxylic acid (11 g, 44.4 mmol) in dimethylformamide (20 ml) were added.

To the resulting solution kept under stirring at −5° C., dicyclohexylcarbodiimide (11 g, 53.4 mmol) and N-hydroxy-benzotriazole (7.2 g, 53.4 mmol) were added.

After 24 hours under stirring at +4° C., the precipitate (dicyclohexylurea) was filtered and the filtrate was evaporated to dryness.

An oil was obtained which was dissolved in ethyl acetate and the solution was washed with an aqueous solution of citric acid at 10%, with an aqueous sodium bicarbonate solution at 10% and with water.

The organic solution, dried on sodium sulphate was evaporated to dryness under vacuum at 40° C.

(N-t.butoxycarbonyl-2-methyl-thiazolidine-4-carbonyl)-L-methionine methyl ester (13.5 g) was thus obtained as oil.

The obtained product was treated at room temperature under nitrogen, with ethyl acetate (45 ml) containing 13% (w/v) of hydrogen chloride.

After 1 hour the solution was evaporated to dryness under vacuum at 35° C.

The residue, after crystallization from isopropyl alcohol diethyl ether, afforded (2-methyl-thiazolidine-4-carbonyl)-L-methionine methyl ester hydrochloride (8.9 g).

$[\alpha]_D^{20} = -94°$ (c=1, $CH_3OH$)
m.p.=115°-116° C.
$R_f$=0.8 (AcOEt:Py:AcOH:$H_2O$=120:10:3:5.5)

EXAMPLE 7

Preparation of (2-methyl-thiazolidin-4-carbonyl)-L-proline methyl ester hydrochloride.

To a solution of L-proline methyl ester hydrochloride (3.68 g, 22.2 mmol) in dimethylformamide (25 ml) kept under stirring at −5° C., N-methyl-morpholine (2.45 ml, 22.2 mmol) and then a solution of N-t.butoxycarbonyl-2-methyl-thiazolidine-4-carboxylic acid (5 g, 20.2 mmol) in dimethylformamide (10 ml) were added.

To the resulting solution kept under stirring at −5° C., dicyclohexylcarbodiimide (5.03 g, 24.4 mmol) and N-hydroxy-benzotriazole (3.29 g, 24.4 mmol) were added.

After 24 hours under stirring at +4° C., the precipitate (dicyclohexylurea) was filtered and the filtrate was evaporated to dryness.

An oil was obtained which was dissolved in ethyl acetate and the solution was washed with an aqueous solution of citric acid at 10%, with an aqueous sodium bicarbonate solution at 10% and with water.

The organic solution, dried on sodium sulphate was evaporated to dryness under vacuum at 40° C.

(N-t.butoxycarbonyl-2-methyl-thiazolidine-4-carbonyl)-L-proline methyl ester (5.47 g) was obtained by crystallization of the residue from ethanol at 10% (v/v).

$[\alpha]_D^{20} = -139°$ (c=1, $CH_3OH$)
m.p.=105°-106° C.

The obtained product (2.6 g, 7.25 mmol) was treated at room temperature under nitrogen, with ethyl acetate (80 ml) containing 13% (w/v) of hydrogen chloride.

After 15 minute the solution was evaporated to dryness under vacuum at 35° C.

The residue, after crystallization from diethyl ether, afforded (2-methyl-thiazolidine-4-carbonyl)-L-proline methyl ester hydrochloride (1.8 g).

$[\alpha]_D^{20} = -179°$ (c=1, $CH_3OH$)
$R_f$=0.8 (AcOEt:Py:AcOH:$H_2O$=120:10:3:5.5)

EXAMPLE 8

Preparation of (2-methyl-thiazolidin-4-carbonyl)-beta-alanine methyl ester hydrochloride.

The preparation in example 4 was repeated by using 180 g (0.728 mol) of N-t.butoxycarbonyl-2-methyl-thiazolidine-4-carboxylic acid.

The (2-methyl-thiazolidin-4-carbonyl)-beta-alanine methyl ester was crystallized from petroleum ether.

The obtained product [220 g, $[\alpha]_D^{20} = -74°$ (c=1, MeOH), m.p.=62° C.] was treated at room temperature under nitrogen with ethyl acetate (950 ml) containing 13% (v/v) of hydrogen chloride.

After 1 hour the solution was evaporated to dryness under vacuum at 35° C.

The residue, after crystallization from isopropyl alcohol, afforded (2-methyl-thiazolidine-4-carbonyl)-beta-alanine methyl ester hydrochloride (145 g)

$[\alpha]_D^{20} = -93°$ (c=1, MeOH)
m.p.=129°–130° C.
$R_f$=0.74 (AcOEt:Py:AcOH:H$_2$O=120:10:3:5.5)

EXAMPLE 9

Preparation of (2-methyl-thiazolidin-4-carbonyl)-L-methionine methyl ester hydrochloride.

The preparation of example 6 was repeated by using 175 g (0.708 mol) of N-t.butoxycarbonyl-2-methyl-thiazolidine-4-carboxylic acid.

The (2-methyl-thiazolidin-4-carbonyl)-L-methionine methyl ester was crystallized from petroleum ether.

The obtained product [163 g, $[\alpha]_D^{20} = -76°$ (c=1, MeOH), m.p.=65° C.] was treated at room temperature under nitrogen with ethyl acetate (730 ml) containing 13% (v/v) of hydrogen chloride.

After 1 hour the solution was evaporated to dryness under vacuum at 35° C.

The residue, after crystallization from isopropyl alcohol/diethyl ether, afforded (2-methyl-thiazolidine-4-carbonyl)-L-methionine methyl ester hydrochloride (104 g).

$[\alpha]_D^{20} = -100°$ (c=1, MeOH)
m.p.=119°–120° C.
$R_f$=0.8 (AcOEt:Py:AcOH:H$_2$O=120:10:3:5.5)

We claim:

1. A compound of formula

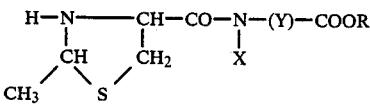

(I)

wherein the group

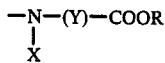

represents the residue of a natural amino acid selected from the group consisting of glycine, alanine, beta-alanine, phenylalanine, isoleucine, methionine, proline, aspartic acid and arginine; R represents a hydrogen atom or a C$_1$–C$_4$ alkyl; and their acid-addition salts with pharmaceutically acceptable organic or inorganic acids.

2. A compound according to claim 1 in which R represents a C$_1$–C$_4$ alkyl.

3. A pharmaceutically acceptable acid-addition salt of a compound according to claim 1 in which R represents a C$_1$–C$_4$ alkyl.

4. A compound according to claim 1 in which the group

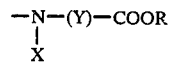

represents the residue of an amino acid selected from methionine, beta-alanine and proline.

5. A method for the preventive and curative treatment of pathologic syndromes due to the depletion of the glutathione (GSH) content in the parenchymal organs and in the mesenchymal cellular population, said method consisting in administering a therapeutically effective amount of a compound of claim 1.

6. A method for the preventive or curative treatment of toxic or toxinfective hepatopathy, of respiratory affections having infective origin or originated by inhalation of extraneous substances, of arthritis, of degenerative cardiopathy during chemotherapy or of central or peripheral neuropathy due to depletion of glutathione (GSH) levels, said method consisting in administering a therapeutically effective amount of a compound according to claim 1.

7. A pharmaceutical composition for the preventive and curative treatment of pathologic syndromes due to the depletion of the glutathione (GSA) in the parenchymal organs and in the mesenchymal cellular population wherein said composite contains an effective amount of an active ingredient of the compound of claim 1.

8. A pharmaceutical composition for the preventive or curative treatment of toxic or toxinfective hepatopathy, of respiratory affections having an infective origin originating by inhalation of extraneous substances, arthritis, degenerative cardiopathy developed during chemotherapy or of central or peripheral neuropathy due to depletion of gluathione (GSH) levels containing an effective amount of an active ingredient of the compound of claim 1.

* * * * *